(12) United States Patent
Khalifa et al.

(10) Patent No.: US 9,855,255 B1
(45) Date of Patent: Jan. 2, 2018

(54) SUBSTITUTED NAPHTHYRIDINYL HYDRAZINES AS ANTI-LIVER CANCER AGENTS

(71) Applicant: KING SAUD UNIVERSITY, Riyadh (SA)

(72) Inventors: Nagy Mahmoud Hassan Khalifa, Riyadh (SA); Mohamed A. Al-Omar, Riyadh (SA); Abd El-Galil E. Amr, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/607,397

(22) Filed: May 26, 2017

(51) Int. Cl.
C07D 201/06 (2006.01)
A61K 31/15 (2006.01)
A61K 31/4375 (2006.01)

(52) U.S. Cl.
CPC .......... *A61K 31/4375* (2013.01); *A61K 31/15* (2013.01); *C07D 201/06* (2013.01)

(58) Field of Classification Search
CPC ... C07D 201/06; A61K 31/15; A61K 31/4375
See application file for complete search history.

(56) References Cited

U.S. PATENT DOCUMENTS

| | | | |
|---|---|---|---|
| 7,446,112 B2 | 11/2008 | Grootenhuis | |
| 8,513,420 B2 | 8/2013 | Mazik | |
| 9,309,241 B2 | 4/2016 | Angibaud et al. | |
| 9,388,192 B2 | 7/2016 | Czardybon et al. | |
| 2008/0293712 A1 | 11/2008 | Wissner et al. | |
| 2010/0179143 A1 | 7/2010 | Adams et al. | |

FOREIGN PATENT DOCUMENTS

CN 103113369 5/2013

OTHER PUBLICATIONS

Eweas et al., 23(1) Med. Chem. Res. 76-86 (2014) (CAS Abstract) (Year: 2014).*

A. Madaan et al., "Anti-inflammatory activity of a naphthyridine derivative (7-chloro-6-fluoro-N-(2-hydroxy-3-oxo-lphenyl-3-(phenylamino)propyl)-4-oxo-1-(prop-2-yn-l-yl)-1,4-dihydro-1,8-naphthyridine-3-carboxamide) possessing in vitro anticancer potential", International Immunopharmacology (2013), vol. 15, pp. 606-613.

Shi et al., "Benzophenone-nucleoside derivatives as telomerase inhibitors: Design, synthesis, and anticancer evaluation in vitro and in vivo", Eur J Med Chem., (2016), 29(124), 729-739.

Y. Tsuzuki et al., "Synthesis and structure-activity relationships of 3-substituted 1,4-dihydro-4-oxo-1-(2-thiazolyl)-1,8-naphthyridines as novel antitumor agents", (2004) Bioorg Med Chem Lett., 14(12):3189-3193.

Y. Tsuzuki et al., "Synthesis and structure-activity relationships of novel 7-substituted 1,4-Dihydro-4-oxo-1-(2-thiazolyl)-1,8-naphthyridine-3-carboxylic acids s as Antitumor Agents. Part 2", (2004) J Med Chem, 47:2097-2109.

* cited by examiner

*Primary Examiner* — Timothy R Rozof
(74) *Attorney, Agent, or Firm* — Richard C. Litman

(57) ABSTRACT

The substituted naphthyridinyl hydrazine compounds as anti-liver cancer agents are anti-liver cancer agents that inhibit proliferative pathways of cancer cells, thereby exhibiting potent in vitro and in vivo anticancer activity. The compounds have the formula:

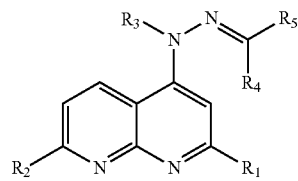

wherein $R_1$ and $R_2$ each are selected independently from hydrogen, mercapto, and $C_1$-$C_5$-alkyl, preferably methyl, ethyl, propyl, isopropyl or halogen; $R_3$ and $R_4$ each are selected independently from hydrogen, alkyl or halogen; and $R_5$ is selected from substituted or unsubstituted aryl, more preferably from substituted phenyl, naphthyl, and substituted or unsubstituted heteroaryl, more preferably from furyl, pyrrolyl, thienyl, imidazolyl, thiadiazolyl, pyridinyl, pyridazinyl, pyrimidinyl, benzothiazolyl, oxadiazolyl or sugar moieties. These agents exert their action through topoisomerase II inhibition.

14 Claims, 14 Drawing Sheets

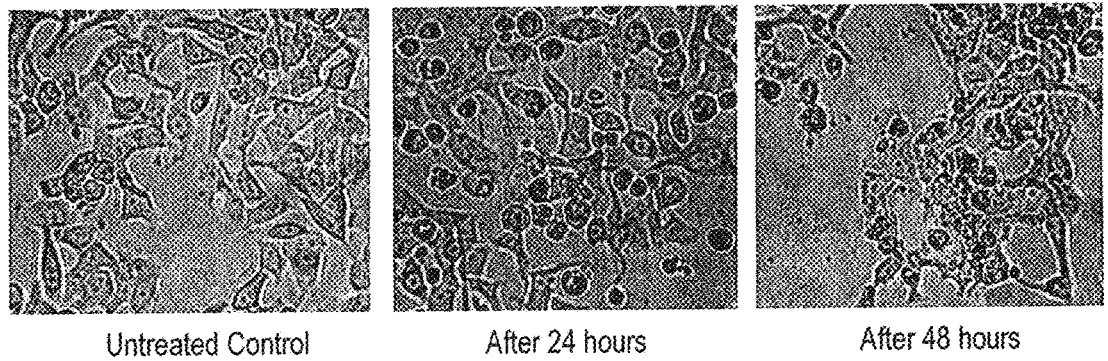
FIG. 7A  Untreated Control
FIG. 7B  After 24 hours
FIG. 7C  After 48 hours
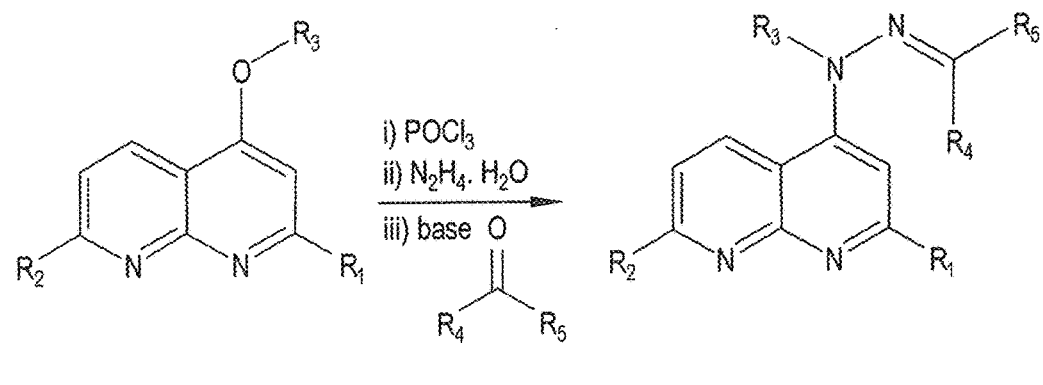
FIG. 8

SUBSTITUTED NAPHTHYRIDINYL HYDRAZINES AS ANTI-LIVER CANCER AGENTS

BACKGROUND OF THE INVENTION

1. Field of the Invention

The present invention relates to compounds useful as anti-liver cancer agents, and in particular, to substituted naphthyridinyl hydrazine compounds as anti-liver cancer agents and methods for their preparation.

2. Description of the Related Art

In spite of the tremendous efforts in discovery and development of new anticancer drugs, cancer remains one of the leading disease causes of death worldwide. The World Health Organization recently estimated that the number of cancer deaths worldwide would reach 13.1 million by 2030.

One key characteristic of cancer cells is their highly proliferative nature. Consequently, inhibition of proliferative pathways continues to be considered an effective strategy to fight cancer. Therapeutic strategies presently used in clinical practice for cancer treatments generally focus on cytotoxic drugs as the main form of chemotherapy for cancer.

Cytotoxic drugs are very heterogeneous chemical compounds that treat cancer primarily by their toxic effect on cells that are rapidly growing and dividing. Because cancer cells often undergo rapid growth and proliferation, they are preferentially killed by these agents.

Compounds belonging to the naphthyridine class have been reported to possess anticancer activities. SNS-595, an anticancer naphthyridine analog that acts by inducing DNA damage, is presently in phase III clinical trial. Due to the diverse side effects of traditional cytotoxic anticancer drugs, much attention has recently been paid to the discovery and development of new, more selective anticancer agents that inhibit proliferative pathways of cancer cells.

DNA topoisomerases are a group of ubiquitous enzymes that are essential for cell survival and proliferation in both prokaryotic and eukaryotic organisms. The mammalian enzyme topoisomerase II (topo II) has the ability to change the DNA topology by breaking the double helix of DNA and allowing a chain transition. It is well established that blocking the effects of this enzyme terminates further DNA replication. The indispensable nature of these enzymes makes them prime targets as potent antitumor agents. Compounds such as naphthyridine derivative Vosaroxin (Formerly SNS-595, AG-7352, AT-3639, or Voreloxin) (shown in FIG. 2) have been found to exhibit potential anticancer activity. Vosaroxin is currently subject to clinical development. The mechanism of this drug is believed to be topo II inhibition. Vosaroxin has demonstrated promising therapeutic potential for the prevention and treatment of cancer.

Accordingly, this knowledge led to the development of new antitumor agents able to block activity of the topo II enzyme. A number of drugs were developed following this strategy of inhibiting topo II enzymes. Such agents found to provide useful clinical application include etoposide, doxorubicin, ellipticine and amsacrine.

While such agents have been found effective for some applications, there is still a need for new anti-cancer agents for different applications. Thus, substituted naphthyridinyl hydrazine compounds as anti-liver cancer agents solving the aforementioned problems are desired.

SUMMARY OF THE INVENTION

The substituted naphthyridinyl hydrazine compounds as anti-liver cancer agents are anti-liver cancer agents that inhibit proliferative pathways of cancer cells, thereby exhibiting potent in vitro and in vivo anticancer activity. The compounds have the formula:

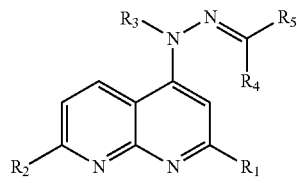

wherein $R_1$ and $R_2$ each are selected independently from hydrogen, mercapto, and $C_1$-$C_5$-alkyl, preferably methyl, ethyl, propyl, isopropyl or halogen; $R_3$ and $R_4$ each are selected independently from hydrogen, alkyl or halogen; and $R_5$ is selected from substituted or unsubstituted aryl, more preferably from substituted phenyl, naphthyl, and substituted or unsubstituted heteroaryl, more preferably from furyl, pyrrolyl, thienyl, imidazolyl, thiadiazolyl, pyridinyl, pyridazinyl, pyrimidinyl, benzothiazolyl, oxadiazolyl or sugar moities. These agents exert their action through topoisomerase II inhibition.

Preferred embodiments include the specific compound of formula 1 referred to below as the "target compound," or "compound 6," having the following structure:

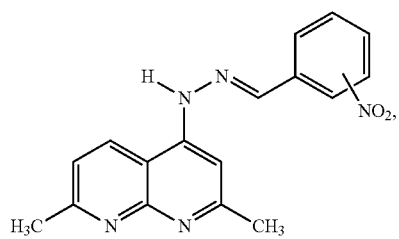

the specific compound of formula 1 referred to below as "compound 8b," having the following structure:

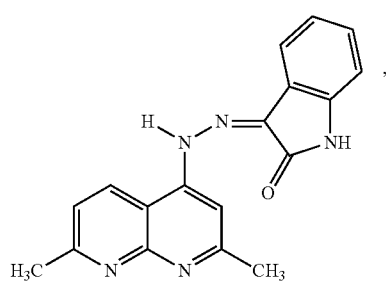

and the specific compound of formula 1 referred to below as "compound 8c," having the following structure:

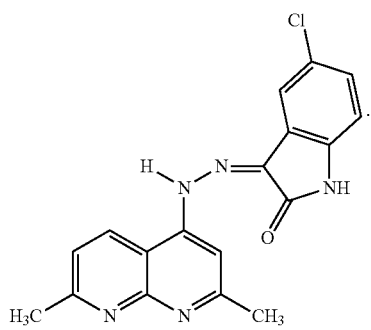

These and other features of the present invention will become readily apparent upon further review of the following specification and drawings.

BRIEF DESCRIPTION OF THE DRAWINGS

FIGS. 7A, 7B, and 7C are phase contrast micrographs showing morphological changes in HepG2 cells treated with compound 6 (a substituted naphthyridinyl hydrazine according to the present invention) over time, from before administration for the untreated control (FIG. 7A), 24 hours after administration (FIG. 7B), and 48 hours after administration of compound 6 (FIG. 7C).

FIG. 8 is a reaction scheme showing synthesis of substituted naphthyridinyl hydrazines according to the present invention Similar reference characters denote corresponding features consistently throughout the attached drawings.

DETAILED DESCRIPTION OF THE PREFERRED EMBODIMENTS

The substituted naphthyridinyl hydrazine compounds as anti-liver cancer agents are anti-liver cancer agents that inhibit proliferative pathways of cancer cells, thereby exhibiting potent in vitro and in vivo anticancer activity. The compounds have the formula:

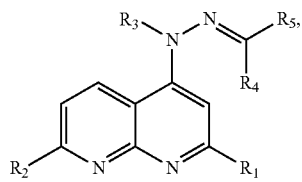

wherein $R_1$ and $R_2$ each are selected independently from hydrogen, mercapto, and $C_1$-$C_5$-alkyl, preferably methyl, ethyl, propyl, isopropyl or halogen; $R_3$ and $R_4$ each are selected independently from hydrogen, alkyl or halogen; and $R_5$ is selected from substituted or unsubstituted aryl, more preferably from substituted phenyl, naphthyl, and substituted or unsubstituted heteroaryl, more preferably from furyl, pyrrolyl, thienyl, imidazolyl, thiadiazolyl, pyridinyl, pyridazinyl, pyrimidinyl, benzothiazolyl, oxadiazolyl or sugar moities. These agents exert their action through topoisomerase II inhibition.

Preferred embodiments include the specific compound of formula 1 referred to below as the "target compound," or "compound 6," having the following structure:

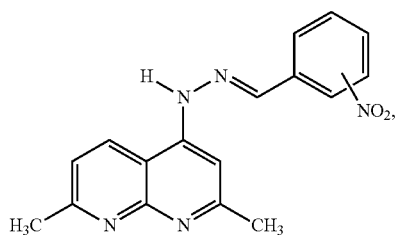

the specific compound of formula 1 referred to below as "compound 8b," having the following structure:

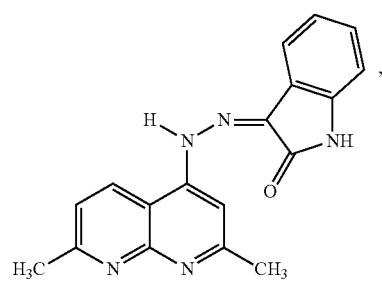

and the specific compound of formula 1 referred to below as "compound 8c," having the following structure:

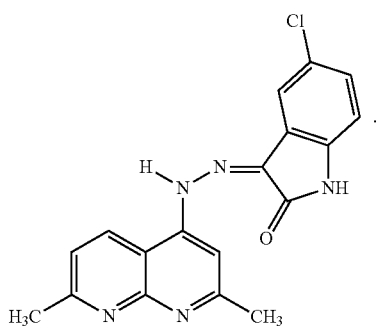

8c

Surprisingly, it was found that compounds according of the above formulas possess anticancer activity, superior to the activity of known anticancer agents. In particular, it was found that some of the compounds described above exhibit an activity 1.5 times greater than that of 5-fluorouracil or doxorubicin, which are used as standard anticancer agents in the treatment of cancer.

Figure 1:
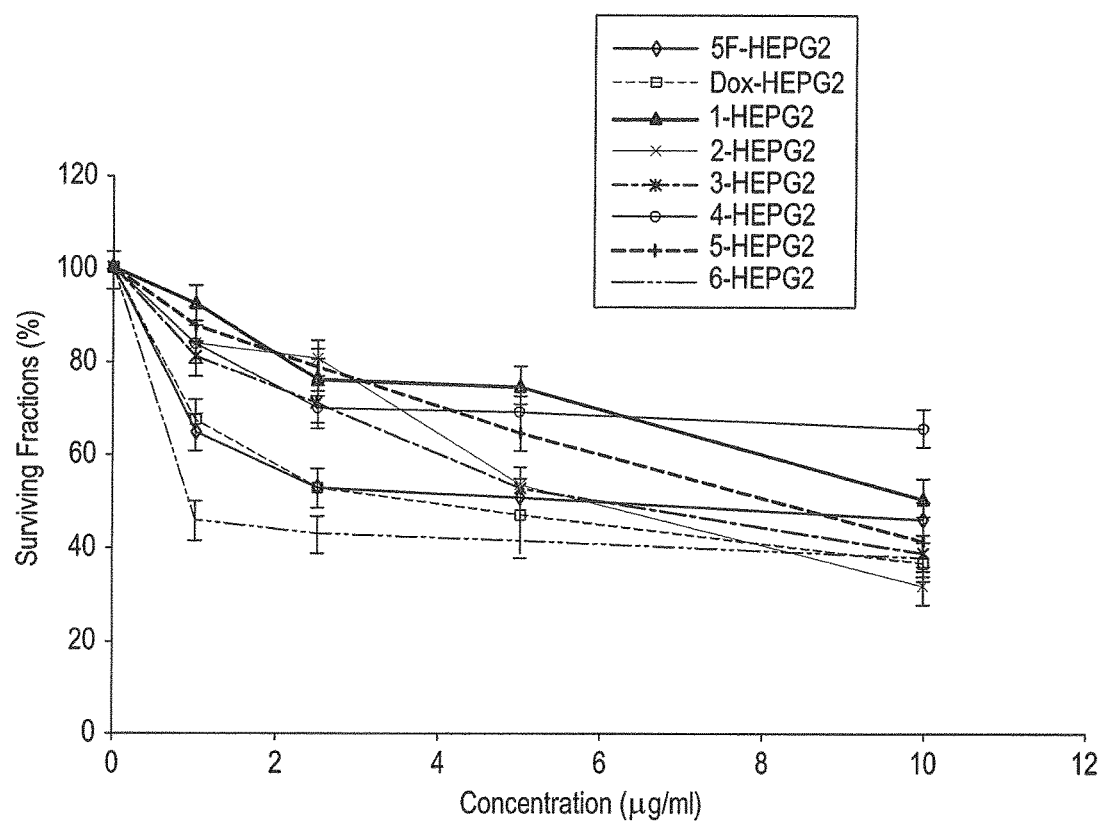
FIG. 1 is a chart evaluating cytotoxic effects of substituted naphthyridinyl hydrazines according to the present invention on liver cancer HEPG2, as compared to prior art treating agents 5-Fluorouracil (5FU or 5F) and Doxorubicin (DOX or Dox), at different concentrations.
Figure 2:
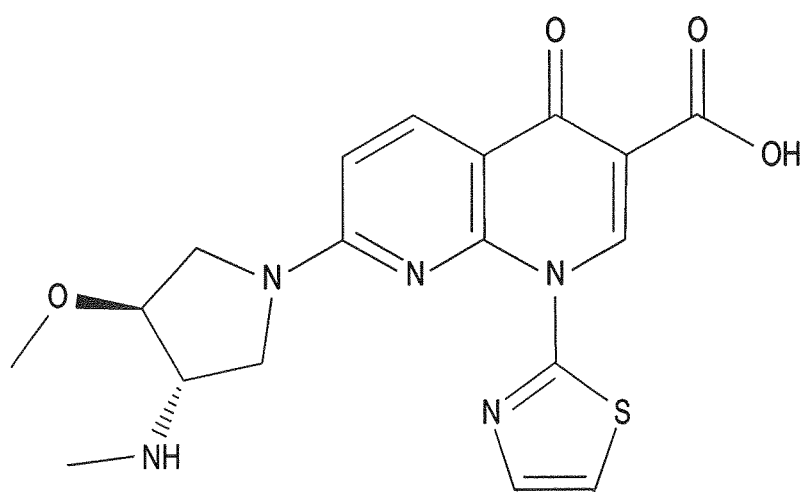
FIG. 2 is the structural formula of Vosaroxin, a naphthyridinyl anti-liver cancer agent of the prior art.

Vosaroxin, a naphthyridine derivative that is an anticancer drug in (phase III) clinical trials, exerts its action through topoisomerase II inhibition. FIG. 2 shows the chemical structure of Vosaroxin.

The investigation showed that Vosaroxin has high affinity for docking in the binding site of topoisomerase II. Vosaroxin fits seamlessly into the active site of topoisomerase II and recorded a high binding energy score (DG=−95.16 kcal/mol) by forming 8 hydrogen bonds with the amino acid residues at the binding site. Six of the hydrogen bonds were with the protein portion of topoisomerase II, and two of the hydrogen bonds were with the DNA segment. This indicates that Vosaroxin is intercalating with the DNA segment. The two hydrogen bonds formed with the DNA segment are both connected to the amino group of the Dc-9 and N-8 of the naphthyridine ring and O—$CH_3$ of the 7-pyrolidine substituent of Vosaroxin, while the remaining six hydrogen bonds are connected to Lys-723 (four bonds) and Gln-726 (two bonds) amino acids of topoisomerase II. See Table 1.

Figure 3A:
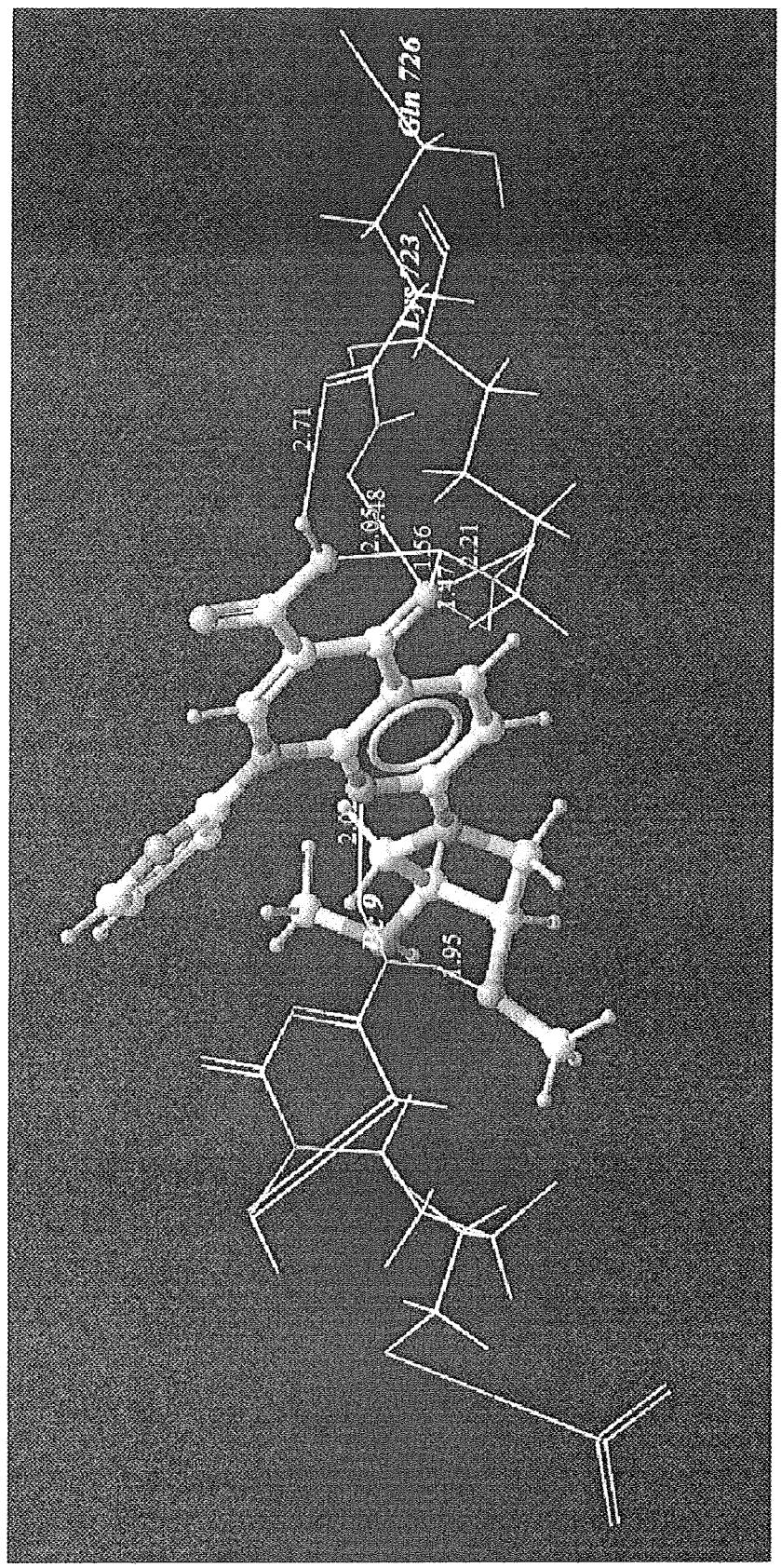
FIG. 3A is model showing binding of Vosaroxin (formerly Voreloxin, an anti-liver cancer agent of the prior art) with Topoisomerase II, and showing intermolecular hydrogen.
Figure 3B:
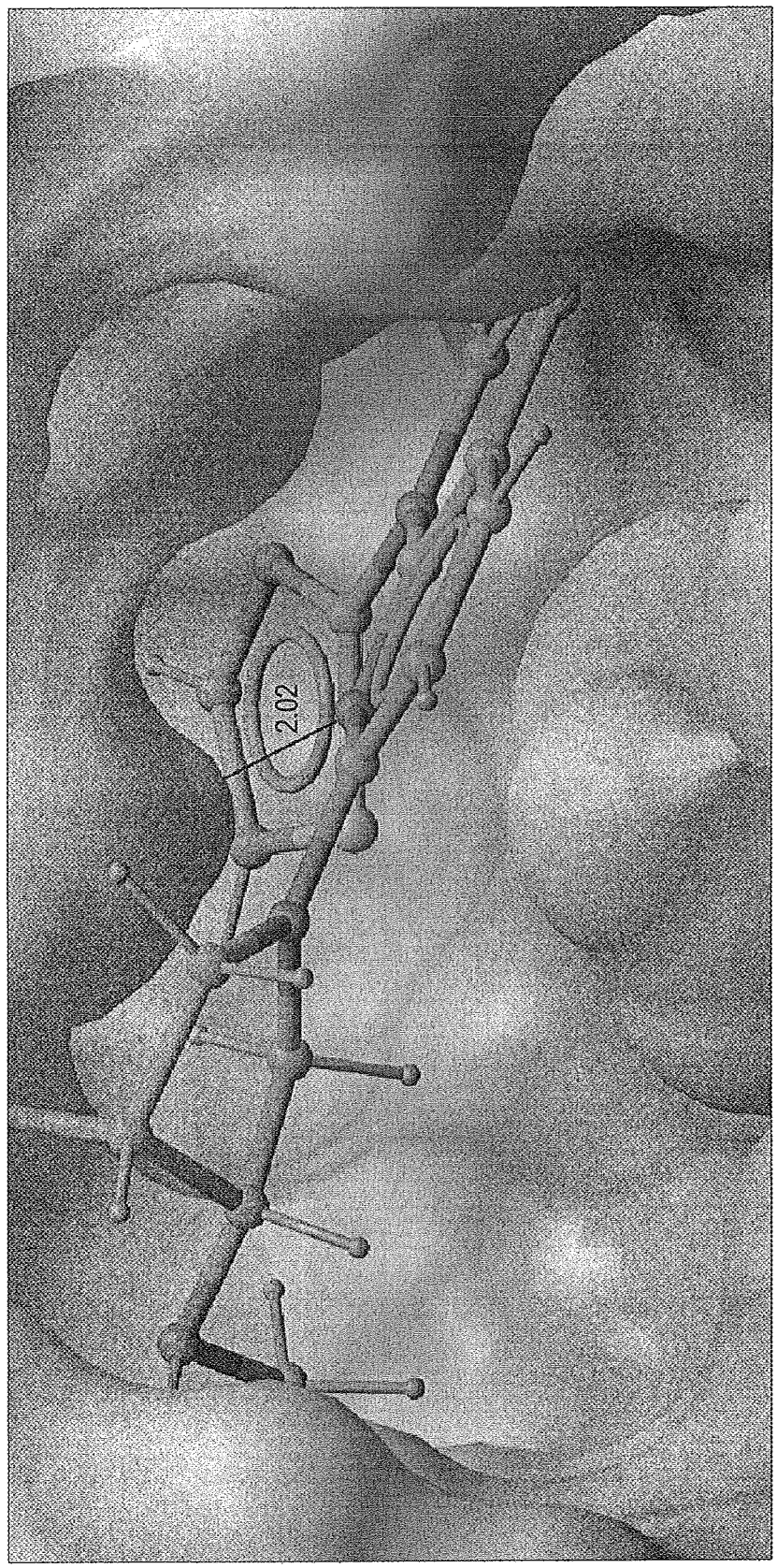
FIG. 3B is a 3-D model of the interaction between Voreloxin, an anti-liver cancer agent of the prior art, and Topoisomerase II.

A binding model of Vosaroxin with Topoisomerase II shows intermolecular hydrogen bonding. See FIG. 3A. A 3-D model also represents the interaction between Vosaroxin and Topoisomerase II. See FIG. 3B.

In contrast, the present compound 6 recorded a docking score of −65.50 Kcal/mol, forming 1 hydrogen bond with the amino acid residues at the binding site. See Table 1.

TABLE 1

Comparison of Vosaroxin and Compound 6 Docking Energy with Topoisomerase II

| Compound ID | Docking score (Kcal/mol) | No. of Hydrogen bonds | Amino acid residues forming hydrogen bonds in A° |
| --- | --- | --- | --- |
| Vosaroxin | −95.16 | 8 | a K723 hz1 -- m M o3: 1.47 |
|  |  |  | a K723 hz2 -- m M o2: 2.05 |
|  |  |  | a K723 hz2 -- m M o3: 1.56 |
|  |  |  | a K723 hz3 -- m M o3: 2.21 |
|  |  |  | a Q726 he22 -- m M o3: 2.48 |
|  |  |  | c C9 h42 -- m M n2: 2.02 |
|  |  |  | c C9 h41 -- m M o4: 1.95 |
|  |  |  | a Q726 oe1 -- m M h4: 2.71 |
| Compound 6 | −65.50 | 1 | d T10 o1p -- m M h10: 2.67 |

Other compounds of formula 1 have also been shown to similarly bind with Topoisomerase II. In particular, a binding model of compound 8b with Topoisomerase II shows intermolecular hydrogen bonding.

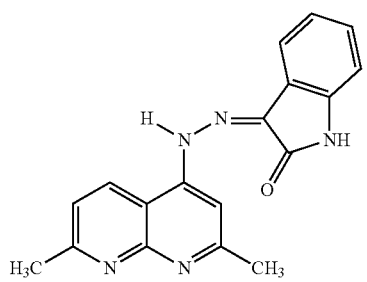

8b

Figure 4A:
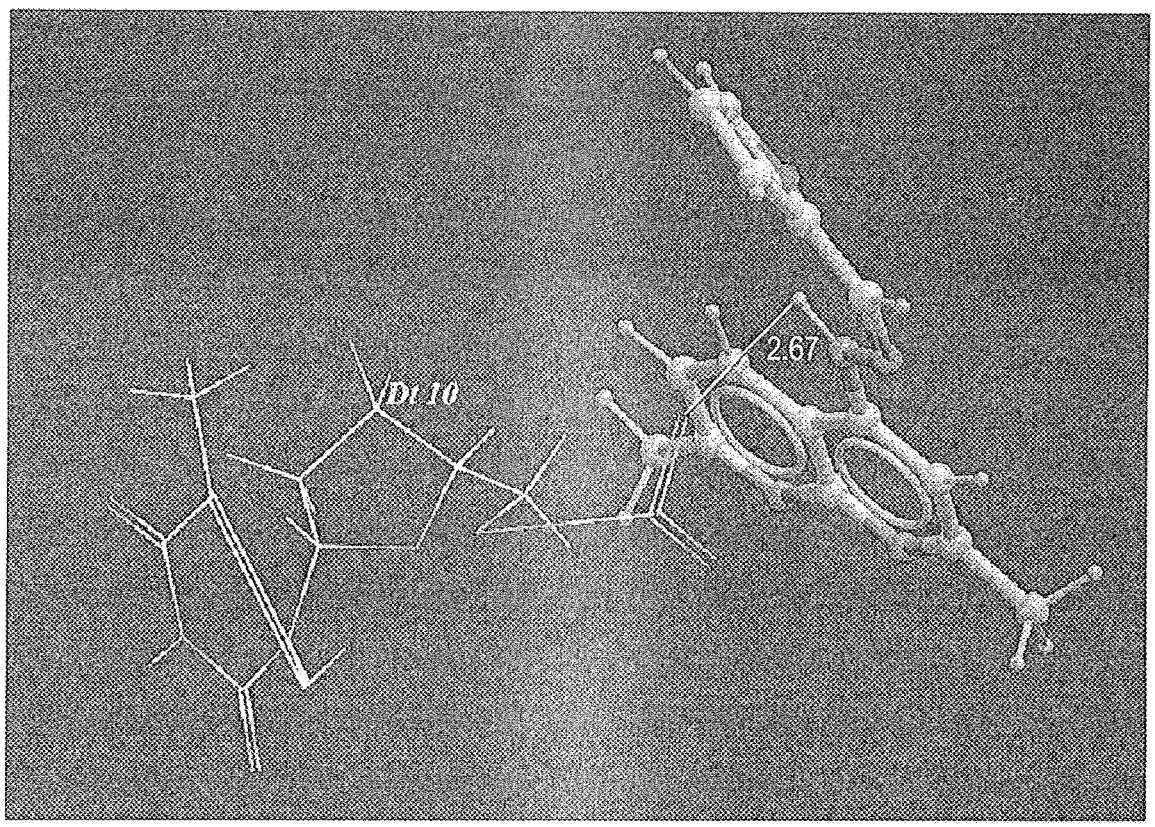
FIG. 4A is model showing binding of compound 8b (a substituted naphthyridinyl hydrazine according to the present invention) with Topoisomerase II, and showing intermolecular hydrogen.

See FIG. 4A. And a 3-D model represents the interaction between compound 8c and Topoisomerase II.

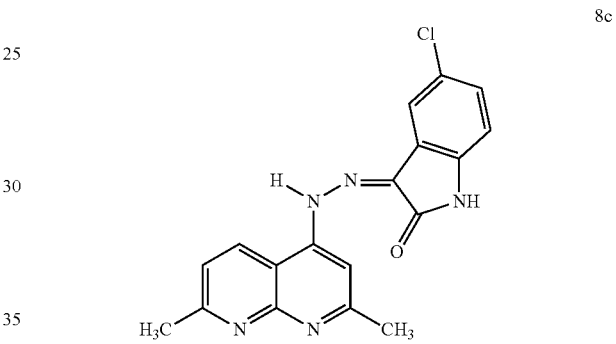

8c

Figure 4B:
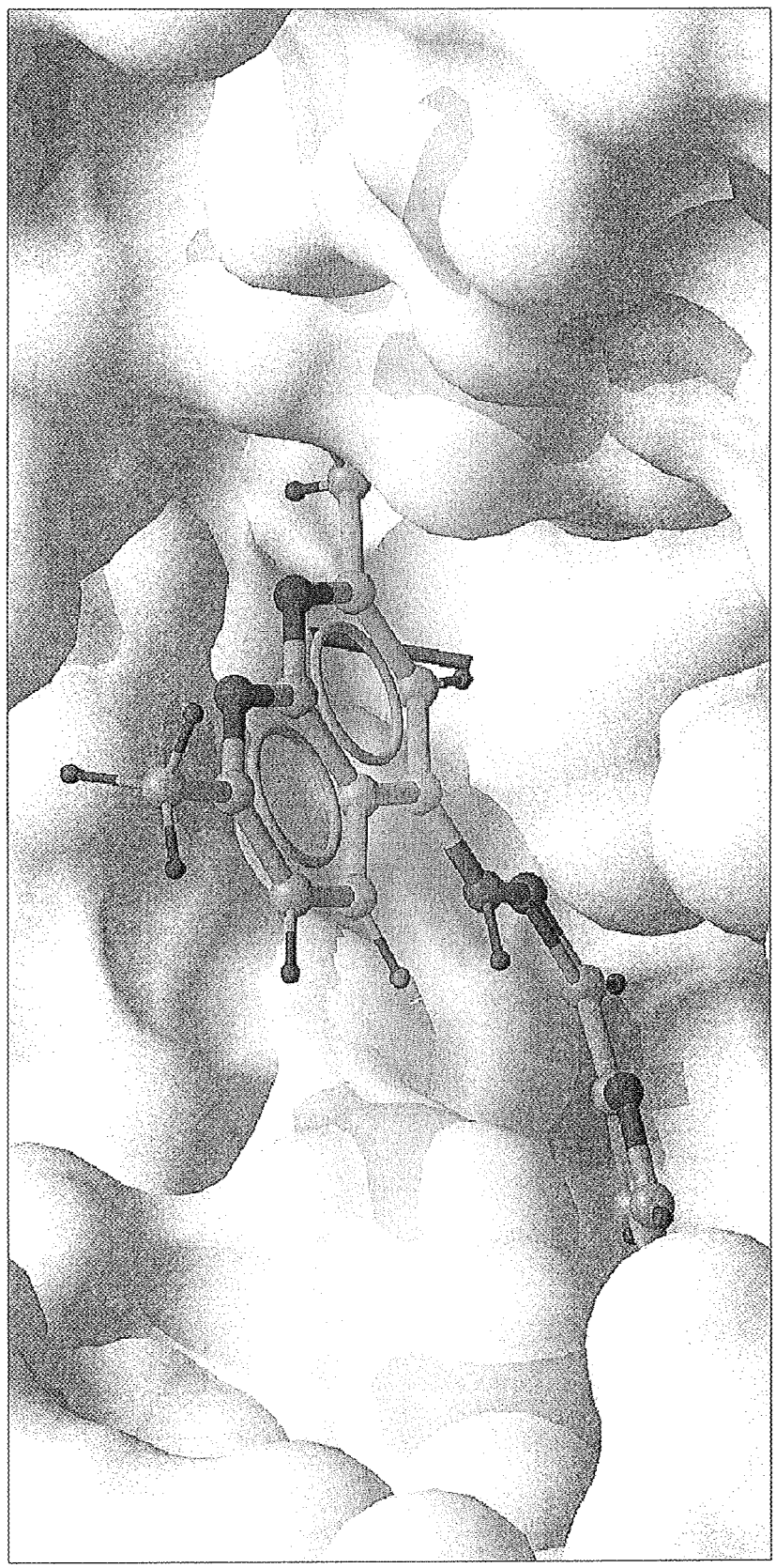
FIG. 4B is a 3-D model of the interaction between compound 8b and Topoisomerase II.

See FIG. 4B.

The substituted naphthyridinyl hydrazine compounds are synthesized according to the method shown in the reaction scheme of FIG. 8. In the scheme shown in FIG. 8, $R_1$, $R_2$, $R_3$, $R_4$ and $R_5$ each are independently selected from the group including hydrogen, halogen, $C_1$-$C_5$-alkyl, aryl, heteroaryl, naphthyl, mercapto, alkylthio, or alkylamino, or wherein $R_3$ and $R_4$ are members of a ring system in the resulting formula 1 compound. The proper naphthyridine derivative 2 (i.e., providing the $R_1$, $R_2$, and $R_3$ substituents desired in the product structure) is reacted with an oxychloride (here, phosphorous oxychloride) at a temperature ranging from room temperature to about 210° C., preferably about 160-180° C., followed by treatment with base in a suitable solvent. Suitable solvents include, for example, ethyl alcohol, methyl alcohol, butyl alcohol, dioxane, tetrahydrofuran and toluene. Methyl alcohol gives 4-substituted-1,8-naphthyridine derivatives in good yield, followed by reaction with ketonic compounds (providing the desired $R_4$ and $R_5$ substituents) at temperatures ranging from room temperature to 110° C., preferably 80° C., in the presence of a catalytic amount of base.

Suitable bases include triethylamine, potassium carbonate, or piperidine in a suitable solvent, such as ethyl alcohol, methyl alcohol, isopropyl alcohol, butyl alcohol, dioxane, toluene and acetic acid, preferably ethyl alcohol, to afford the target product 1.

The product 1 can be purified by recrystallization from suitable solvent, for example, ethyl alcohol, methyl alcohol, benzene, acetic acid or dimethyl formamide.

Male albino mice, weighing 18-20 g each, were used in a study. The mice were divided into three main groups, as follows. Group 1 is the untreated control group (5 mice); Group 2 is divided into two subgroups (5 mice in each subgroup), treated with either 5-FU (5-Fluorouracil) or DOX (Doxorubicin) as reference anticancer drugs. Group 3 is divided into ten subgroups (5 mice for each subgroup) and treated with the present substituted naphthyridinyl hydrazine compounds. The mice were housed in wide cages and well aerated rooms, and fed standard diets and clean water. Blood collection from the animals was done with heparinized cannula, and the mice were left alive.

For treatment, in Group 1, each mouse was given a single intraperitoneal (i.p.) injection of 0.1 mL DMSO; in Group 2, each mouse was given a single i.p. injection of 0.1 mL containing 12 mg/kg body weight of 5-FU or DOX dissolved in sterile water; and in Group 3, each mouse was given a single intraperitoneal injection of 0.1 mL containing 12 mg/kg body weight of the selected furan derivatives dissolved in 0.01% DMSO. Blood was collected after 7 days from all mouse groups.

The biochemical effects of formula 1 compounds on some liver enzymes in mouse blood serum was studied. Effects on aspartate and alanine aminotransferases (AST and ALT), and alkaline phosphatase (ALP), were examined using a blood auto analyzer, Olympus AV 400, Japan. Moreover, albumin, globulins, creatinine, total lipids, cholesterol, triglycerides, and bilirubin were evaluated, in comparison to treatment using 5-FU or DOX. Statistical analysis of the results was performed using Chi-square values (SPSS computer program). The results are reported in Table 2.

TABLE 2

Effect of 5-FU, Dox, and Compound 6 on mice serum

| Biochemical Parameters | Control | Mice Groups 5-FU P< | Doxorubicin P< | Compound 6 P< |
|---|---|---|---|---|
| Alanine amino transferase ALT (IU/ml) | 43.5 ± 2.03 | 51.47 ± 9.02 0.001 | 59.26 ± 12.03 0.001 | 46.09 ± 6.13 n.s. |
| Aspartate amino transferase AST (IU/ml) | 108.32 ± 4.19 | 130.431 ± 8.92 0.001 | 147.22 ± 16.34 0.001 | 112.81 ± 9.88 n.s. |
| Alkaline phosphatase ALP (k.k./dl) | 18.70 ± 1.10 | 25.48 ± 6.03 0.001 | 30.31 ± 5.14 0.001 | 21.59 ± 3.42 n.s. |
| Total Lipids mg/dl | 323.41 ± 27.1 | 378.2 ± 31.4 0.001 | 21.94 ± 3.4 0.01 | 326.32 ± 19.3 n.s. |
| Cholestrol mg/dl | 94.32 ± 13.5 | 105.9 ± 11.7 0.001 | 109.3 ± 14.2 0.001 | 93.24 ± 19.53 n.s. |
| Triglycerides mg/dl | 108.7 ± 16.8 | 126.5 ± 19.4 0.001 | 137.8 ± 17.10 0.001 | 110.54 ± 17.8 n.s. |
| Bilirubin mg/dl | 0.63 ± 0.04 | 0.75 ± 0.10 0.001 | 0.81 ± 0.19 0.001 | 0.76 ± 0.15 0.01 |
| Albumin mg/dl | 5.63 ± 0.51 | 6.49 ± 0.92 0.01 | 6.37 ± 0.85 0.01 | 7.73 ± 0.52 0.01 |
| Globulin mg/dl | 4.32 ± 0.9 | 5.75 ± 0.8 0.01 | 5.91 ± 0.63 0.01 | 6.25 ± 0.82 0.01 |
| A/G ratio | 1.3 | 1.13 0.01 | 1.078 0.01 | 1.23 0.01 |
| Creatinine mg/dl | 0.69 ± 0.03 | 0.81 ± 0.06 0.01 | 0.78 ± 0.04 0.01 | 0.71 ± 0.21 n.s |

Data are expressed as Mean + S.D.
P < 0.01: significant; P < 0.001: highly significant; n.s.: non significant Biological evaluation of the present substituted naphthyridinyl hydrazine compounds revealed that the compounds possess a remarkable degree of anticancer activity. The results obtained clearly indicate the discovery of a new group of anticancer agents that induce their actions through topoisomerase II inhibition and revealed high affinity of the compounds of formula 1 toward the binding site of topoisomerase II. Therefore, anticancer activity of compounds of formula 1 is comparable to that of 5-FU and DOX. The present substituted naphthyridinyl hydrazine compounds have potential use as anticancer agents, with potency proved to be 5-6-fold more active than traditional anticancer drug 5-Fluorouracil (standard), while causing fewer toxic side effects.

Figure 5A:
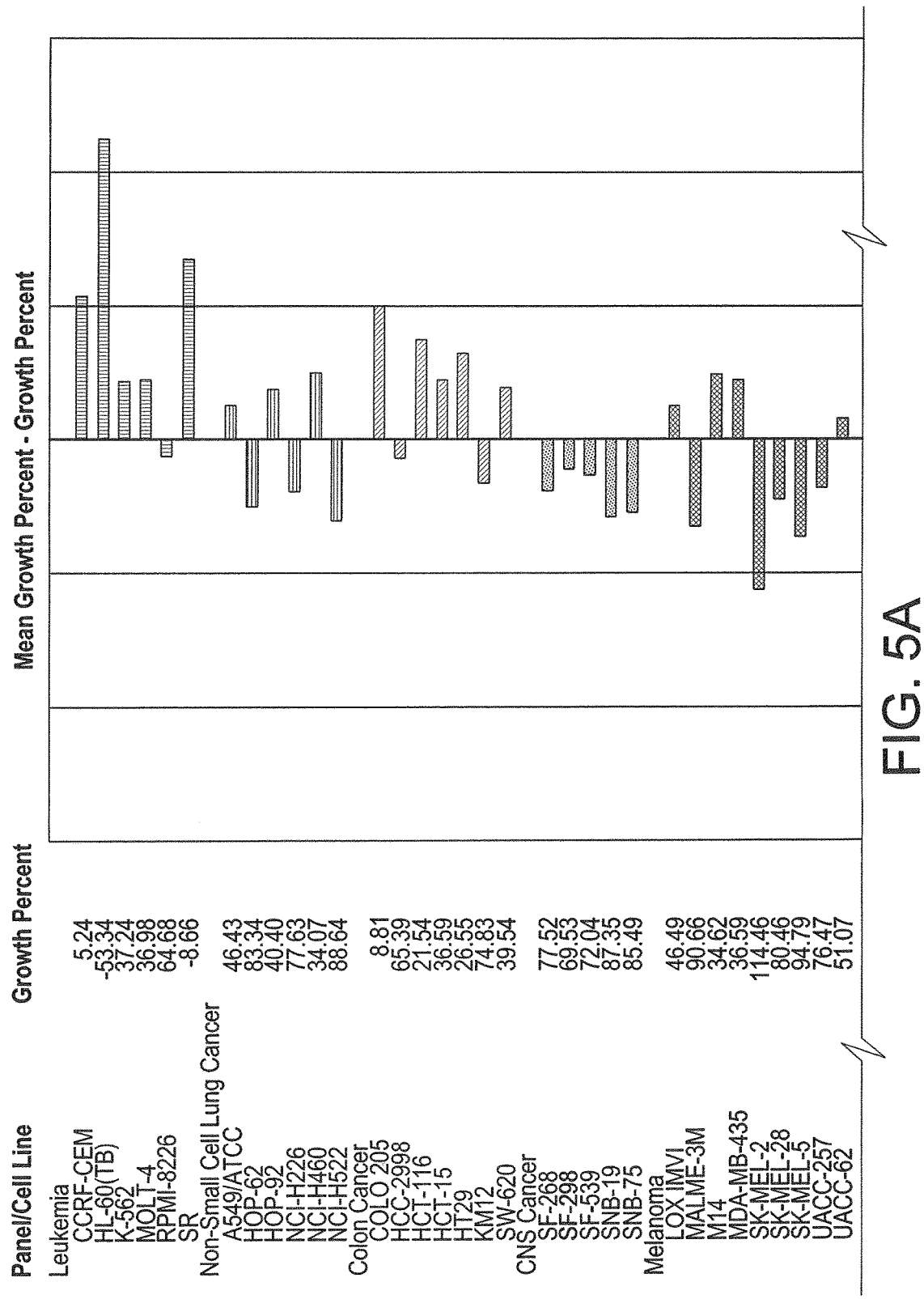
FIGS. 5A and 5B are a chart showing results of single-dose screening for various human cancer cell lines treated with compound 6 (a substituted naphthyridinyl hydrazine according to the present invention).
Figure 5B:
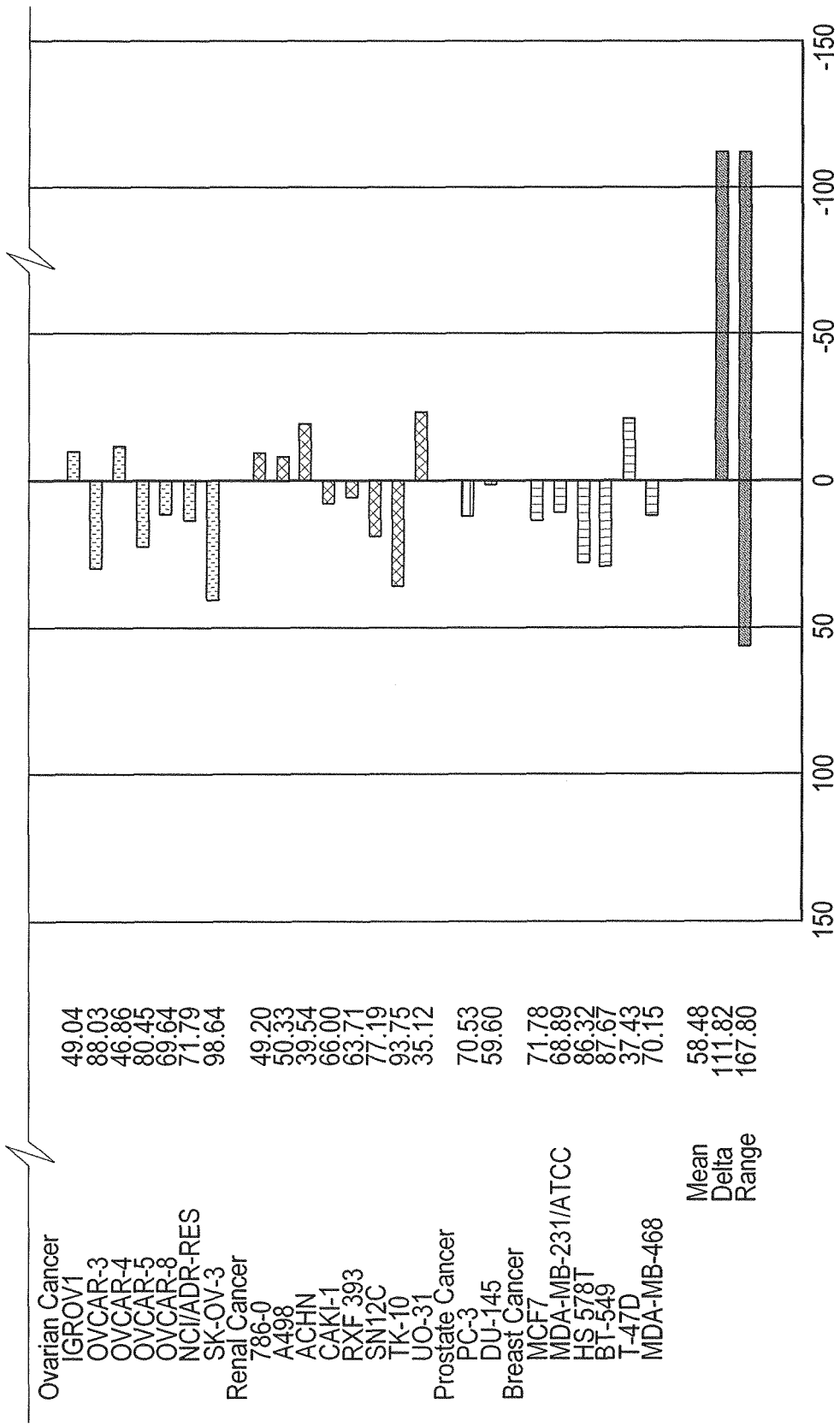
Figure 6A:
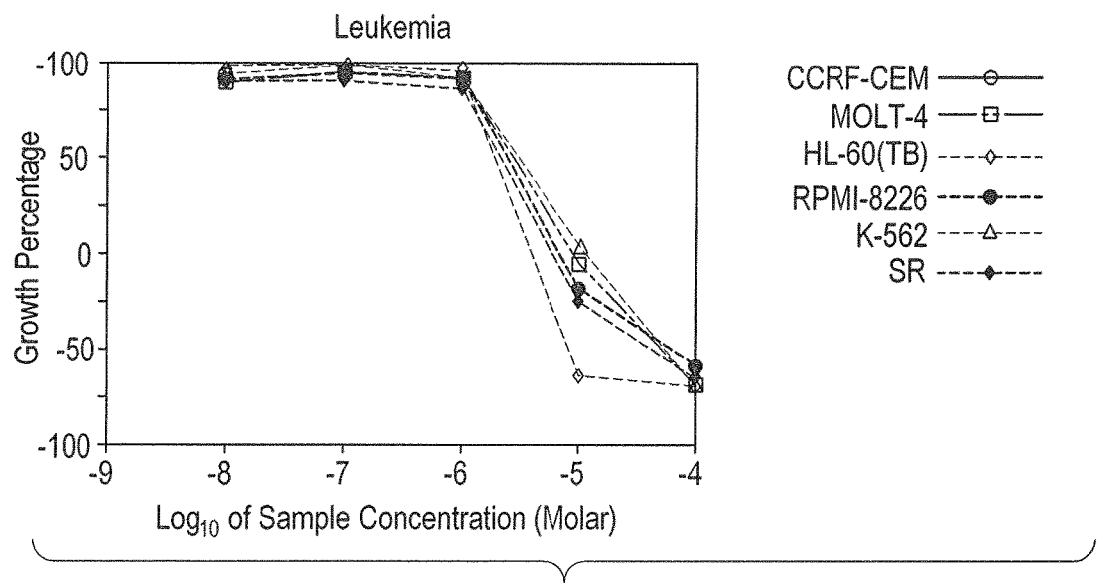
FIGS. 6A, 6B, 6C, 6D, 6E, 6F, 6G, 6H, and 6I show dose response curves for various cancer cell lines treated with compound 6, plotted against the $\log_{10}$ of drug concentration.
Figure 6B:
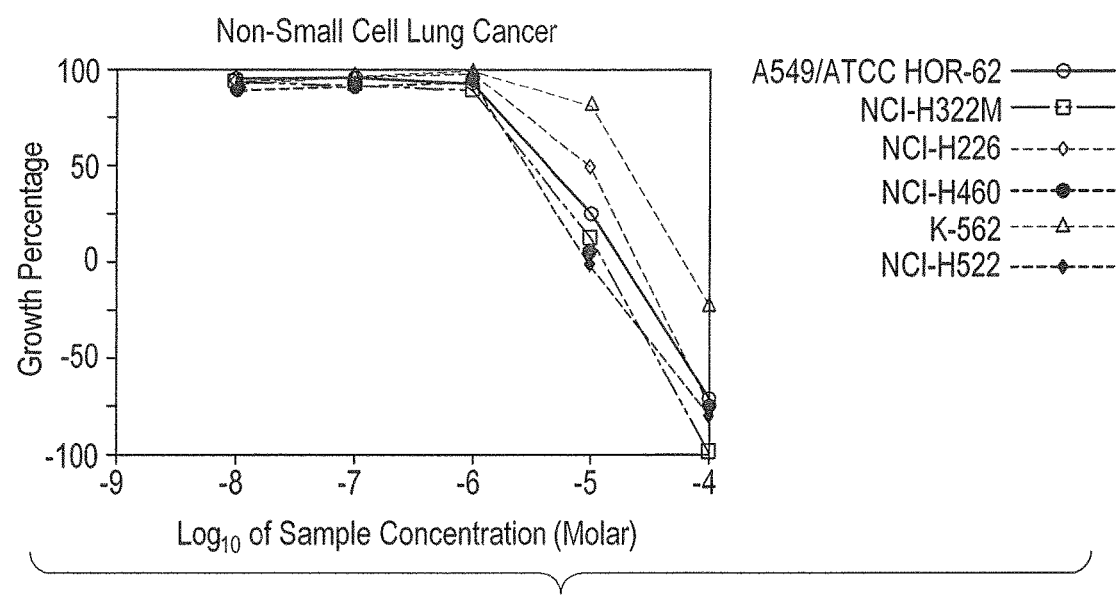
Figure 6C:
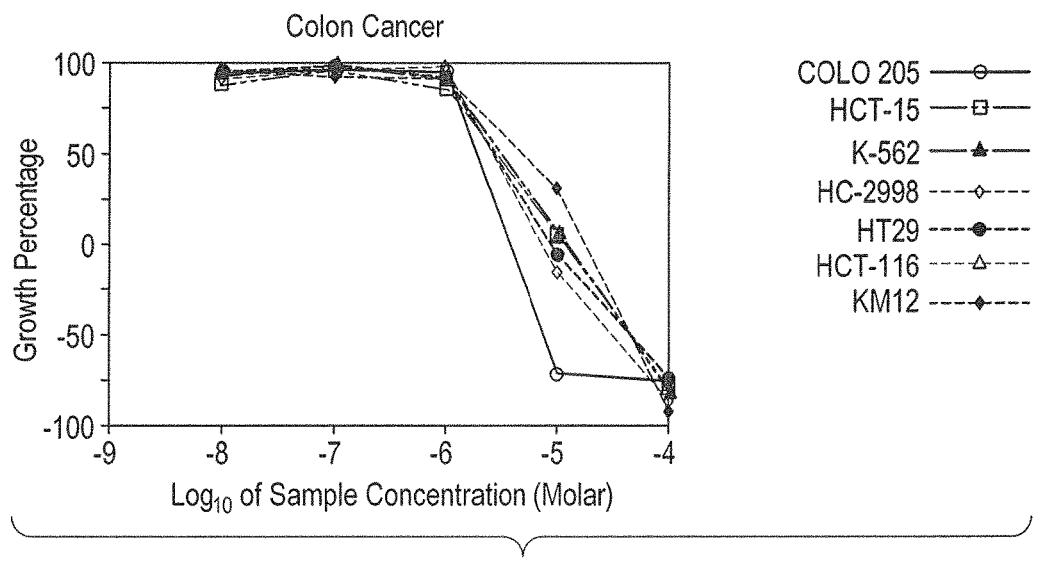
Figure 6D:
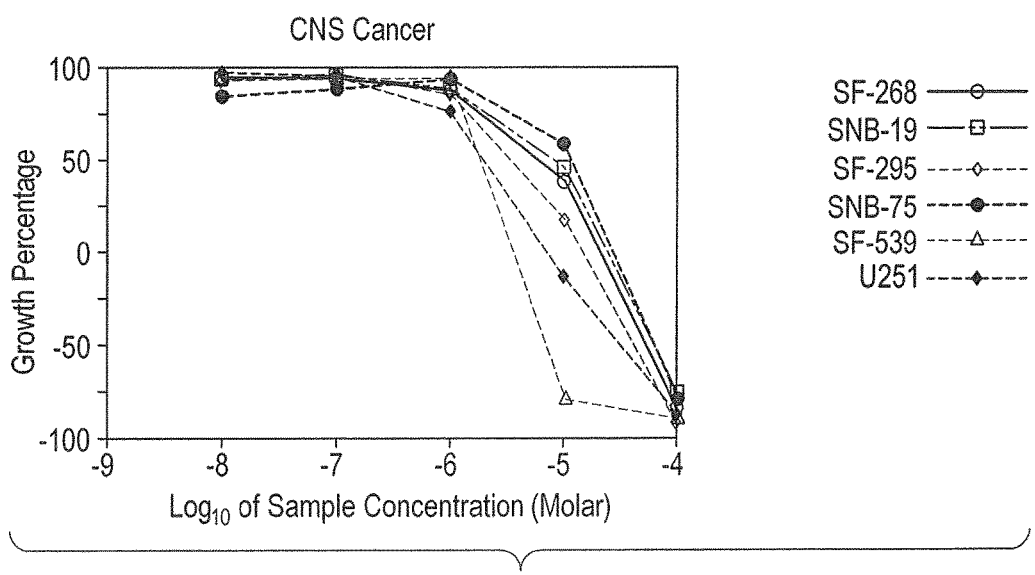
Figure 6E:
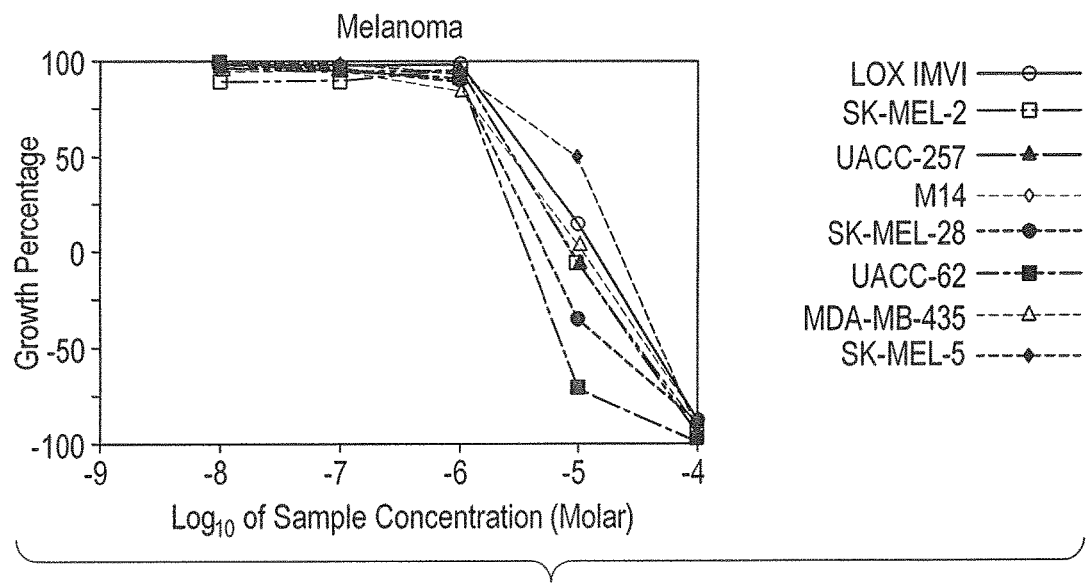
Figure 6F:
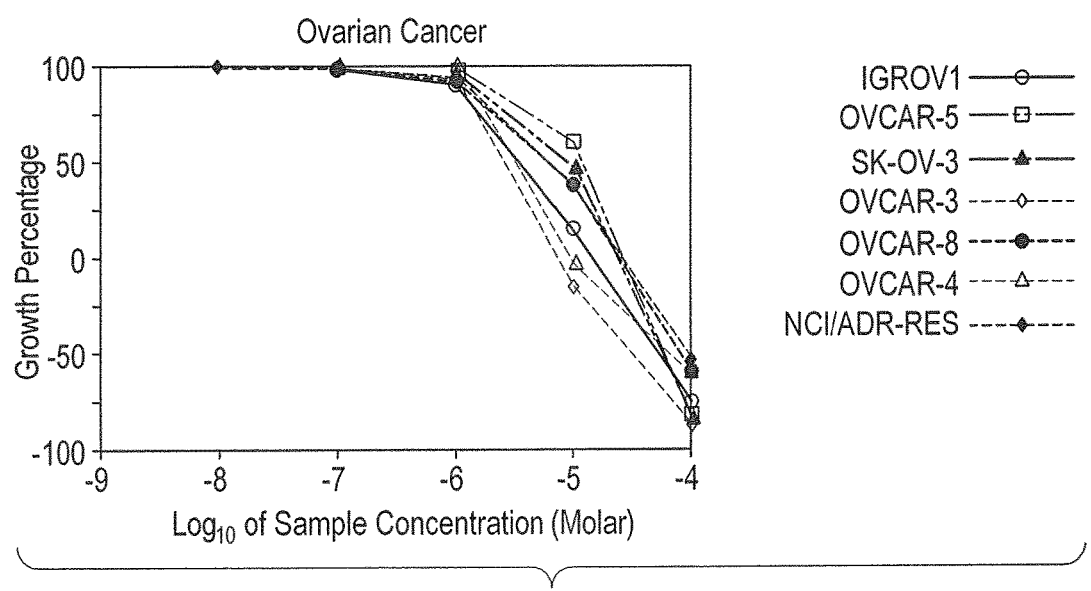
Figure 6G:
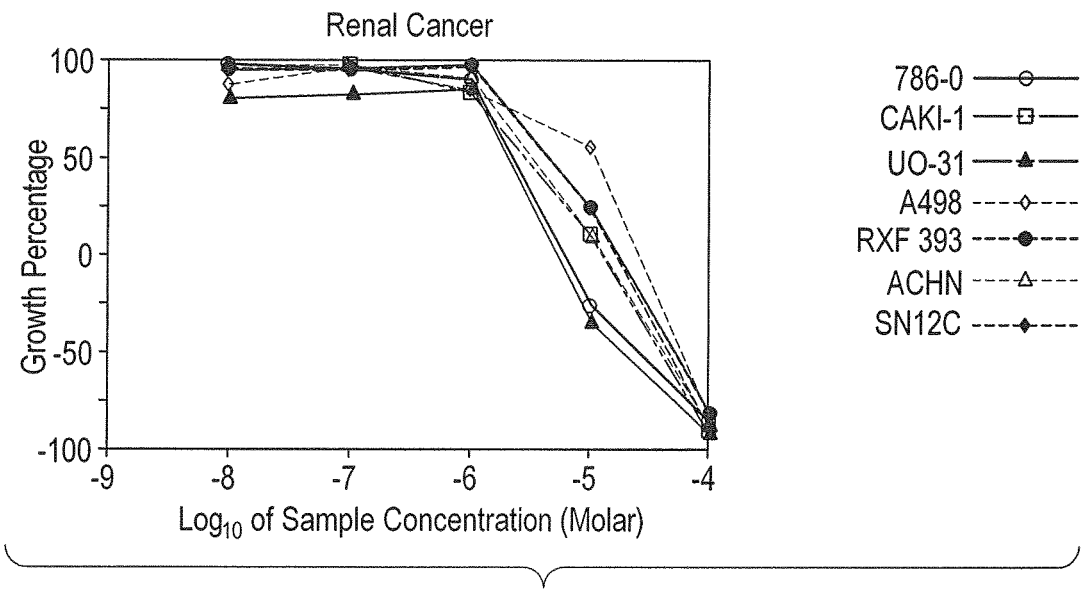
Figure 6H:
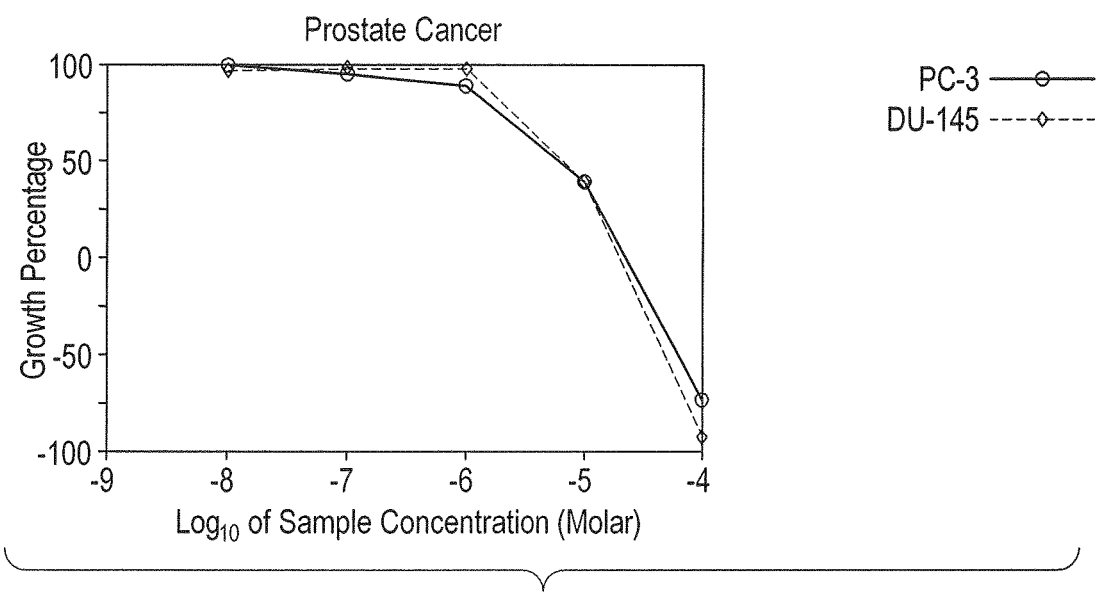
Figure 6I:
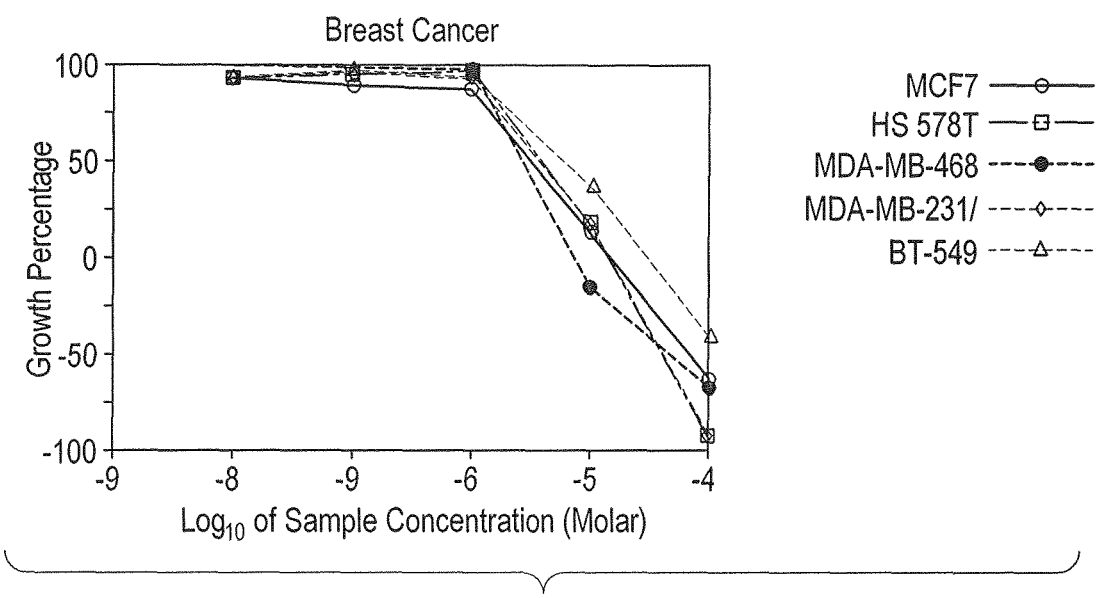

Single-dose screening with Compound 6 against a variety of cancer cell lines (including a variety of leukemia, non-small cell lung cancer, colon cancer, CNS cancer, melanoma, ovarian cancer, renal cancer, prostate cancer, and breast cancer cell lines) typically demonstrated significant decreases in cancer cell growth. See FIGS. 5A and 5B.

The significant growth inhibition against these same cell lines was evaluated further using five different minimal concentrations of compound 6. The presented dose-response curves for each cell lines were plotted for the cytotoxic effect against the $\log_{10}$ drug concentration, as shown in FIGS. 6A-6I. Three parameters were determined, including the molar concentration of the drug that causes 50% growth inhibition ($GI_{50}$), molar concentration that causes total growth inhibition (TGI), and the concentration that kills 50% of the cells ($LC_{50}$).

In the following examples, human cancer cell line HepG2 (Liver) was grown in DMEM media supplemented with 10% bovine serum, 1× penicillin-streptomycin (Sigma-Aldrich) at 37° C. in a humidified chamber with 5% $CO_2$. 5-Flurourasil (Sigma-Aldrich) was used as the reference drug (standard).

Cells were seeded (1×105 cells/well in triplicate) in a 96-well flat-bottom plate (Becton-Dickinson Lab ware) a day before treatment and grown. Stocks of all extracts/compounds (1.0 mg/ml) were made with 5% DMSO (Sigma-Aldrich), and further working solutions (100 μg/ml) were prepared in serum-free culture media. Cells were treated with four different doses (2, 6.2, 12.5, and 25 μg/ml; in triplicate) of the compounds in complete growth media, including reference drug, and further incubated for 48 hours.

On day 2 of treatment, cell proliferation and viability test was performed using TACS MTT Cell Proliferation and Viability Assay Kit (TACS), as per manufacturer's instructions. The relationship between surviving fraction and compound concentration was plotted to obtain the survival curve of cancer cell lines. The response parameter calculated was the $IC_{50}$ value, which corresponds to the concentration required for 50% inhibition of cell viability.

TABLE 3

Comparison of cytotoxic activity on liver HEPG2 cancer cell lines

| Compd. | $IC_{50}$ |
|---|---|
| Compound 6 | 0.885 μg/ml |
| Fluorouracil | 5 μg/ml |
| Doxorubicin | 3.56 μg/ml |

Fat free human serum albumin (HSA), calf thymus DNA (sodium salt, average molecular weight 1×106), RPMI 1640 medium, fetal bovine serum (FBS), MTT dye, trypsin EDTA solution, ethidium bromide, Tris base (Tris-(hydroxymethyl)-amino-methane-hydrogen chloride) and agarose were purchased from Sigma-Aldrich (St. Louis, Mo., USA). All other chemicals used for analysis were also obtained from Sigma-Aldrich (St. Louis, Mo., USA).

The cells were seeded in 6-well plates and allowed to adhere at 37° C. in a $CO_2$ incubator. After 24 h, each well was treated with 10 μg compound and incubated for the indicated time. After 24 and 48 hrs, the cells were imaged by phase contrast microscope (Olympus CLX 41) to visualize morphological changes in HepG2 cells. See FIGS. 7A-7C.

The precise instructions for pharmaceutical administration of the compounds and agents according to the present subject matter necessarily depend on the requirements of the individual case, the nature of treatment, and of course the treating physician.

Example 1

(E)-2-(2-Substituted Arylidene)-1-(2,7-disubstituted Naphthyridinyl) Derivative

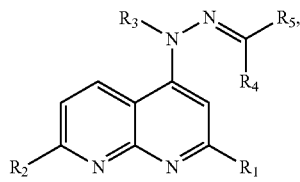

Ketonic derivatives (10 mmol) and a catalytic amount of acetic acid were added to a suspension of the intermediate 3 (10 mmol) (see FIG. 8) in dry ethanol 30 ml. The reaction mixture was refluxed for about 3 hours. Reaction completion was monitored by TLC. The reaction mixture was concentrated under reduced pressure. The crystalline product was collected by filtration, dried and crystallized from methanol to give the required product of formula 1. Yield 73%, mp: 231-233° C.; IR (KBr, cm$^{-1}$) $v_{max}$: 3221, 1665; $^1$H NMR (DMSO-d$_6$) δ: 2.59 (s, 6H), 6.90-8.73 (m, 8H), 9.63 (s, 1H); $^{13}$C NMR (DMSO-d$_6$) δ: 23.91, 107.72, 119.23, 121.46, 125.11, 128.19, 130.94, 131.01, 132.85, 133.87, 134.96, 142.58, 154.82, 157.16, 157.79, 159.77; MS: m/z 355 (M$^+$) consistent with the molecular formula, ($C_{17}H_{15}BrN_4$).

Example 2

(E)-2-(2-Nitrobenzylidene)-1-(2,7-dimethyl-1,8-naphthyridin-5-yl)hydrazine (Compound 6)

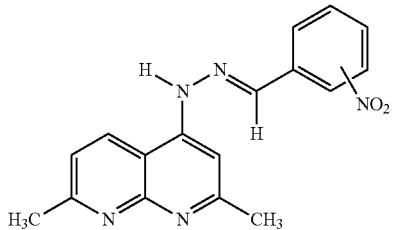

To a solution of hydrazide derivative (10 mmol) in absolute ethyl alcohol (30 mL), was added o-nitrobenzaldehyde (10 mmol) and catalytic amount of piperidine. The reaction mixture was refluxed for about 5 h (Reaction completion was monitored by TLC), then left to cool. The solid precipitate formed was collected by filtration, dried, and recrystallized from methyl alcohol to afford the target product of formula 6. Yield 76%, mp: 255-256° C.; IR (KBr, cm$^{-1}$) $v_{max}$: 3210 (NH), 1624 (C=N); $^1$H NMR (DMSO-d$_6$) δ: 2.61 (s, 6H, 2CH$_3$), 6.85-8.14 (m, 8H, ArH+N=CH), 9.76 (s, 1H, NH, exchangeable); $^{13}$C NMR (DMSO-d$_6$) δ: 23.87, 110.34, 120.54, 121.18, 123.95, 126.32, 130.09, 131.86, 134.40, 134.79, 145.01, 148.62, 154.89, 157.47, 158.01, 160.12; Mass spectrum, m/z (I$_{rel}$, %): 321 (15) [M]$^+$, consistent with the molecular formula ($C_{17}H_{15}N_5O_2$). Anal. Calcd. for $C_{17}H_{15}N_5O_2$ (321.33): C, 63.54; H, 4.71; N, 21.79. Found: C, 63.41; H, 4.59; N, 21.65.

Example 3

(3Z)-3-[2-(2,7-Dimethyl-1,8-naphthyridin-4-yl)hydrazinylidene]-1,3-dihydro-2H-indol-2-one (8b) and (3Z)-5-chloro-3-[2-(2,7-dimethyl-1,8-naphthyridin-4-yl)hydrazinylidene]-1,3-dihydro-2H-indol-2-one (Compound 8)

In the general procedure, a stirred solution of hydrazide 1 (5 mmol), and indoline-2,3-dione or 5-chloroindoline-2,3-dione (5 mmol) in acetic acid (20 mL) was refluxed for 1-3 h. The reaction mixture was cooled to room temperature, poured into crushed ice and the solid product was filtered off, washed with ethanol, dried and recrystallized from (AcOH-ether) to afford the target compounds 8b and 8c, respectively.

Example 4

(3Z)-3-[2-(2,7-Dimethyl-1,8-naphthyridin-4-yl)hydrazinylidene]-1,3-dihydro-2H-indol-2-one Compound 8b

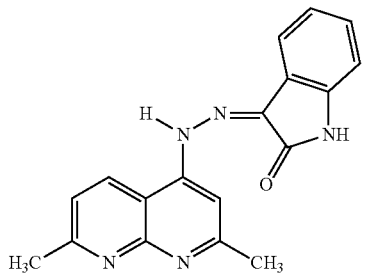

Yield 83%, mp >300° C.; IR (KBr, cm$^{-1}$) $v_{max}$: 3238, 3190 (2NH), 1667 (C=O), 1610 (C=N); $^1$H NMR (DMSO-d$_6$) δ: 2.60 (s, 6H, 2CH$_3$), 6.90-8.12 (m, 7H, ArH), 9.65, 10.26 (2s, 2H, 2NH, exchangeable); $^{13}$C NMR (DMSO-d$_6$) δ: 24.05, 110.28, 118.21, 120.47, 121.58, 124.01, 124.45, 129.37, 131.25, 132.74, 134.42, 147.02, 155.43, 157.61, 158.10, 159.12, 167.23; Mass spectrum, m/z (I$_{rel}$, %): 317 (34) [M]$^+$, consistent with the molecular formula ($C_{18}H_{15}N_5O$). Anal. Calcd. for $C_{18}H_{15}N_5O$ (317.34): C, 68.13; H, 4.76; N, 22.07. Found: C, 67.98; H, 4.63; N, 21.89.

Example 5

(3Z)-5-Chloro-3-[2-(2,7-dimethyl-1,8-naphthyridin-4-yl)hydrazinylidene]-1,3-dihydro-2H-indol-2-one Compound 8c

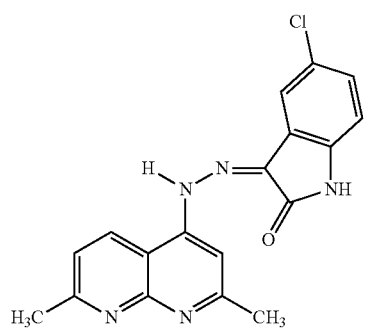

Yield 71%, mp >300° C.; IR (KBr, cm$^{-1}$) $v_{max}$: 3245, 3195 (2NH), 1668 (C=O), 1620 (C=N); $^1$H NMR (DMSO-d$_6$) δ: 2.63 (s, 6H, 2CH$_3$), 6.90-8.15 (m, 6H, ArH), 9.17, 10.38 (2s, 2H, 2NH, exchangeable); $^{13}$C NMR (DMSO-d$_6$) δ: 24.01, 110.36, 119.22, 120.52, 123.05, 124.12, 129.46, 130.01, 131.38, 132.81, 134.29, 145.02, 155.48, 157.42, 158.14, 159.10, 167.43; Mass spectrum, m/z ($I_{rel}$, %): 351 (12) [M]$^+$, consistent with the molecular formula (C$_{18}$H$_{14}$ClN$_5$O). Anal. Calcd. for C$_{18}$H$_{14}$ClN$_5$O (351.79): C, 61.46; H, 4.01; N, 19.91. Found: C, 61.37; H, 3.87; N, 19.77.

Example 6

Measurement of Potential Cytotoxicity by SRB Assay

Cells were plated in 96-well flat-bottom plate (10$^4$ cells/well) and grown for 24 h before treatment with the target compound(s) to allow attachment of cells to the wall of the plate. Different concentrations of the compound under test (0, 1, 2.5, 5, 10 μg/mL) were added to the cell monolayer. Triplicate wells were prepared for each individual dose. Monolayer cells were incubated with the compound(s) for 48 h at 37° C. and in an atmosphere of 5% CO$_2$. Cultures were then fixed with trichloroacetic acid and stained for 30 min with 0.4% (w/v) sulforhodamine B (SRB) dissolved in 1% acetic acid. Unbound dye was removed by four washes with 1% acetic acid, and protein-bound dye was extracted with 10 mμ unbuffered Tris base [tris(hydroxymethyl)aminomethane] for determination of optical density in a computer-interfaced, 96-well microtiter plate reader. The SRB assay results were linear with the number of cells and with values for cellular protein measured by both the Lowry and Bradford assays at densities, ranging from sparse subconfluence to multilayered supraconfluence. The signal-to-noise ratio at 564 nm was approximately 1.5 with 1,000 cells per well. The relation between surviving fraction and drug concentration is plotted to get the survival curve of the cancer cell line after the specified compound.

Example 7

Effect of the Formula 1 on Some Biochemical Parameters in Mice

Data obtained in Table 2 presents the liver enzymatic activities (ALT, AST and ALP) in serum of control and treated groups of mice. The results showed that the values recorded for AST and ALT were significantly higher (P<0.001) with 5-FU- and DOX-treated groups of mice than the control. On the other hand, treatment with the new compound caused inverse effects, where some values recorded for AST and ALT were non-significant (n.s.) or slightly higher (P<0.01) in comparison to control. Moreover, the recorded data showed that ALP activities were significantly increased (P<0.001) with the treatment of 5-FU and DOX, while there were no significant changes in ALP activities upon treatment with the new compound.

Example 8

Microscopy Studies

A. The cells were seeded in 6-well plates and allowed to adhere at 37° C. in CO$_2$ incubator. After 24 h, each well was treated with 10 μg of compound 6 and incubated for the indicated time. After 24 and 48 hrs, the cells were imaged by phase contrast microscope (Olympus CLX 41) to visualize morphological changes in HepG2 cells. See FIGS. 7A-7C.

B. Similar studies were done with HeLa cells. Cells were seeded in 6-well plates and allowed to adhere at 37° C. in CO$_2$ incubator. After 24 h, each well was treated with 4.6 μM 2,6P-OLA and incubated for the indicated time. After 12 and 24 h, the cells were imaged by phase contrast microscope (Olympus CLX 41) to visualize morphological changes in HeLa cells.

Example 9

Morphological Analyses

A. Change in HepG2 cells after treatment with compound 6 was studied for morphological variations using the phase contrast microscopy. Changes in surface morphology of the HepG2 cells were observed after 24 and 48 hrs (FIGS. 7A-7C).

B. Change in LeLa cells after treatment with compound 6 was also studied for morphological variations using the phase contrast microscopy. Changes in surface morphology were observed after 12 and 24 hrs to visualize morphological changes in HeLa cells.

Many characteristic features occur in cells undergoing a series of biochemical events during apoptosis. Various morphological changes, such as blebbing, loss of membrane asymmetry, cell shrinkage, nuclear fragmentation, chromatin condensation, and chromosomal DNA fragmentation occur. In FIG. 7B, cells exposed to 10 μg of compound for 24 hours show the onset of apoptotic characteristics, where most of the cells lose their typical branch-shaped morphology and cause shrinking of cell. After 48 hours of exposure, blebbing and loss of basal attachment and membrane asymmetry is markedly seen, as shown in FIG. 7C.

It is to be understood that the present subject matter is not limited to the embodiments described above, but encompasses any and all embodiments within the scope of the following claims.

We claim:

1. A substituted naphthyridinyl hydrazine compound, comprising a compound having the formula:

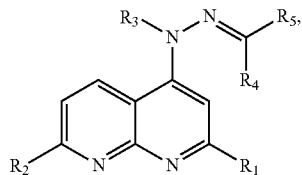

wherein $R_1$ and $R_2$ each are selected independently from the group consisting of hydrogen, mercapto, halogen, and $C_1$-$C_5$ alkyl; $R_3$ and $R_4$ each are selected independently from the group consisting of hydrogen, alkyl and halogen; and $R_5$ is a substituted or unsubstituted aryl or heteroaryl group
Provided that R5 is not furyl.

2. The compound of claim 1, wherein:
$R_1$ and $R_2$ each are selected independently from the group consisting of methyl, ethyl, propyl, and isopropyl; and
$R_5$ is selected from the group consisting of substituted phenyl, naphthyl, furyl, pyrrolyl, thienyl, imidazolyl, thiadiazolyl, pyridinyl, pyridazinyl, pyrimidinyl, benzothiazolyl, and oxadiazolyl.

3. A method of treating a cancer patient, comprising the step of administering an effective amount of the compound of claim 2 to the patient.

4. The method of claim 3, wherein the patient is being treated for liver cancer.

5. A method of treating a cancer patient, comprising the steps of:
obtaining a compound of claim 2;
determining an appropriate dosing regimen for administering the compound to the patient; and
administering the compound to the patient pursuant to the dosing regimen.

6. The method of claim 5, wherein the patient is being treated for liver cancer.

7. A method of preparing a compound according to claim 1, wherein $R_1$ and $R_2$ each are selected independently from the group consisting of hydrogen, mercapto, and $C_1$-$C_5$-alkyl; $R_3$ and $R_4$ each are selected independently from the group consisting of hydrogen, alkyl and halogen; and $R_5$ is an aryl group, a heteroaryl group or a sugar moiety, the method following scheme 1:

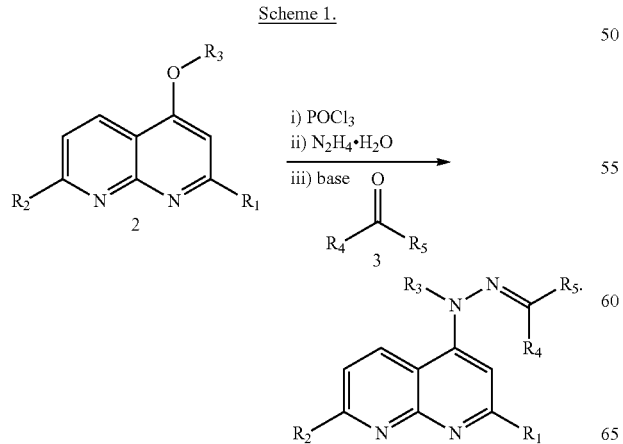

8. A method of preparing the compound according to claim 1, comprising the steps of:
reacting a naphthyridine derivative of formula 2 with oxychloride, followed by addition of a first base in a first solvent; and
adding a ketone of formula 3 in the presence of a catalytic amount of a second base to form the compound of formula 1.

9. The method of claim 8, wherein
the first solvent is at least one solvent selected from the group consisting of ethyl alcohol, methyl alcohol, butyl alcohol, dioxane, tetrahydrofuran, and toluene;
the second base is at least one base selected from the group consisting of trimethylamine, potassium carbonate, and piperidine, the second base being added with a second solvent comprising at least one solvent selected from the group consisting of ethyl alcohol, methyl alcohol, isopropyl alcohol, butyl alcohol, dioxane, toluene, and acetic acid;
and the compound of formula 1 is recrystallized from a third solvent comprising at least one solvent selected from the group consisting of ethyl alcohol, methyl alcohol, benzene, acetic acid, and dimethyl formamide.

10. A method of treating a cancer patient, comprising the step of administering a pharmaceutical composition including an effective amount of the compound according to claim 1 to a patient in need thereof.

11. The method of claim 10, wherein the cancer patient has been diagnosed with liver cancer.

12. The substituted naphthyridinyl hydrazine compound of claim 1, wherein the compound has the formula:

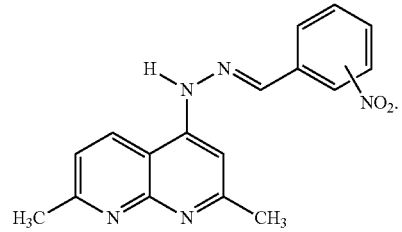

13. The substituted naphthyridinyl hydrazine compound of claim 1, wherein the compound has the formula:

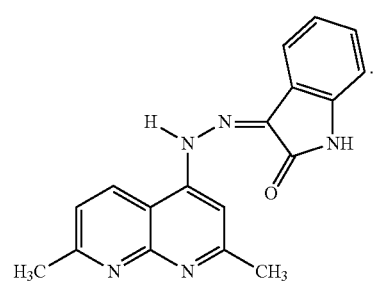 [SMILES: Cc1ccc2c(N/N=C3\C(=O)Nc4ccccc43)cc(C)nc2n1]

14. The substituted naphthyridinyl hydrazine compound of claim 1, wherein the compound has the formula:
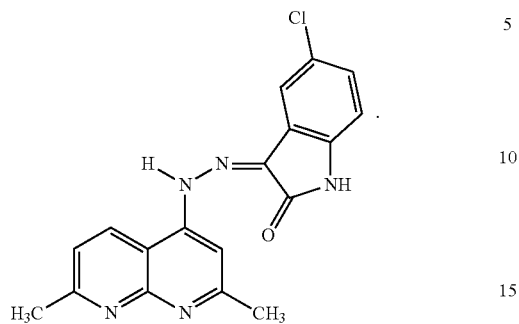
* * * * *